United States Patent [19]
Wendt et al.

[11] Patent Number: 5,186,738
[45] Date of Patent: Feb. 16, 1993

[54] VANADYL COMPOSITIONS AND METHODS FOR APPLYING THE COMPOSITIONS TO PROMOTE PLANT GROWTH

[76] Inventors: Charles W. Wendt, 4518 - 22nd St.; Stanley K. Hicks, 2702 Genoa F4, both of Lubbock, Tex. 79407; Richard B. Baker, 5422 - 44th St., Lubbock, Tex. 79414

[21] Appl. No.: 504,889

[22] Filed: Apr. 5, 1990

[51] Int. Cl.$^5$ .............................. A01N 37/02
[52] U.S. Cl. .................................... 504/192
[58] Field of Search ............................ 71/65, 80, 113

[56] References Cited

U.S. PATENT DOCUMENTS

| | | | |
|---|---|---|---|
| 4,231,788 | 11/1988 | Siemer et al. | 71/113 |
| 4,813,997 | 3/1989 | Kinnersley et al. | 71/66 |
| 4,863,506 | 9/1989 | Young | 71/113 |

FOREIGN PATENT DOCUMENTS

| | | | |
|---|---|---|---|
| 50157167 | 12/1985 | Japan | 71/113 |
| 1060163 | 12/1983 | U.S.S.R. | 71/113 |

OTHER PUBLICATIONS

M. W. Kerr et al., "Attempts to Suppress Photorespiration By Chemical Means", British Plant Growth Regulation Group, Monograph 11, p. 117, (1984).

B. Singh et al., "Effect of Vanadium on Growth, Chemical Composition, and Metabolic Processes of Mature Sugar Beet (*Beta vulgaris* L.) Plants", Plant Physiology, vol. 44, p. 132 (1969).

Daniel I. Arnon et al., "Vanadium as an Essential Element for Green Plants", *Nature*, vol. 72, p. 1039, (Dec. 5, 1953).

B. B. Singh, "Short Communication: Effect of Vanadium on the Growth, Yield, and Chemical Composition of Maze (*Fed. mays* L.)", *Plant and Soil*, vol. 34, p. 209, (1971).

Fouad M. Basiouny, "Distribution of Vanadium and Its Influence on Chlorophyll Formation and Iron Metabolism in Tomato Plants", *Journal of Plant Nutrition*, vol. 7(7), pp. 1059-1073 (1984).

Henrick Saxe et al., "Effect of Vanadate on Bean Leaf Movement, Stomatal Conductance, Barley Leaf Unrolling, Respiration, and Phospatase Activity", Plant Physiology, vol. 68, p. 880, (1981).

Rymar et al., "The Effect of Microelements on the Growth and Yield of Rice", Derwent Publications Ltd., p. 939/635, (1982).

Welch et al., "Plants in Nutrient Solutions Low in Vanadium", *Plant Physiology*, vol. 52, pp. 183-185, (1973).

*Primary Examiner*—Carolyn Elmore
*Assistant Examiner*—B. Bembenick

[57] ABSTRACT

Vanadyl ion compositions for promoting plant growth, especially plant fruits, and the methods for applying the compositions are provided. Specifically, the compositions comprise an organic compound or complex of vanadyl ions and a carrier liquid. Preferably, the organic compound or complex of vanadyl ions is a vanadyl salt of a carboxylic acid, and the pH of the composition ranges from 6 to 8.

The composition is applied to plants, especially monocots and dicots, to promote the growth of the plants. The composition may be sprayed on the foliage of the plants, applied to the earth around the plants, or applied to the roots of the plants by irrigation. The composition should be applied during the growth period of the plants, and particularly from about 21 days before the begining of the reproductive stage of the plant to about 21 days after the begining of the reproductive stage of the plant. The composition should be applied to achieve a treatment rate ranging from about 0.0006 to 0.6 kilograms of vanadium per hectare of plants.

17 Claims, No Drawings

VANADYL COMPOSITIONS AND METHODS FOR APPLYING THE COMPOSITIONS TO PROMOTE PLANT GROWTH

BACKGROUND OF THE INVENTION

The invention relates to vanadyl ion compositions which promote plant growth, especially plant fruit growth, and methods of applying the vanadyl ion compositions. Specifically, the compositions include organic compounds or complexes of vanadium. The vanadium compound or complex provides a source of vanadyl ions which are effective for promoting plant growth. The compositions may be prepared in concentrate form or application form. Effective amounts of the compositions when applied to plants during their growth period, promote plant growth, especially plant fruit growth.

The need for improving the yield and efficiency of horticultural and agricultural crops is becoming more critical as the population of the earth increases and the amount of arable land decreases. Consequently, researchers seek ways to improve the yield of plants through the use of materials which may be used economically as fertilizers, micro-nutrients, and growth promoters for various plants.

Various compositions have been studied as micronutrients and plant growth promoters to increase crop productivity across a wide range of horticultural and agricultural crops. Compositions which include vanadium compounds have been studied in this context, and have shown both beneficial and detrimental effects on plants. Vanadium occurs in the tops of higher plants at levels usually between 0.2 and 4 ppm. For example, vanadium (in the form of a solution of ammonium vanadate at a vanadium concentration of 20 micrograms per liter of nutrient solution) has been shown to be an essential element for unicellular plants such as algae. Arnon et al. 172 NATURE 1039-40 (1953). Further, while vanadium has stimulated growth in maize plants at levels of 0.25 ppm in nutrient solutions, it had no effect on lettuce and tomato plants at levels of 0.05 ppm. Lauchli et al. 15B ENCYCLOPEDIA OF PLANT PHYSIOLOGY 723-26 (1983). A study of the effect of a foliar spray of a vanadyl sulfate solution on leaf growth of sugar beet plants indicated that it decreased leaf growth, but that it increased the amount of reducing sugar in the roots of the sugar beet. Singh et al. 44 PLANT PHYSIOLOGY 1321-27 (1969). The use of vanadium (in the form of vanadyl lactate at concentrations of $10^{-3}$ to $10^{-6}$ molar) as a fertilizer has produced an increase in foliage yield of some higher plants. Kerr et al. Monograph 11 BRITISH PLANT GROWTH REGULATOR GROUP 103-21 (1984).

These studies indicate that vanadium may have some effect on plants, including higher order plants which are of agricultural interest. Whether that effect is beneficial or detrimental appears to depend on the form of the vanadium, the type of plant, and the method and timing of the application. Thus, a need exists to develop an effective vanadium composition and method for applying it that will promote the growth of agriculturally useful plants.

SUMMARY OF THE INVENTION

The invention comprises vanadyl ion compositions which promote plant growth, especially plant fruit growth, when the compositions are effectively applied to the plant. The invention also includes effective methods for applying the compositions to plants to promote their growth. The compositions are prepared in concentrate and application forms. Specifically, the compositions include a carrier agent and a vanadium compound or complex which provides vanadyl ions in an effective concentration when the composition is applied to plants. The vanadyl ions have beneficial effects on the plant growth, particularly plant fruit growth. Preferably, the vanadium compound or complex is a vanadyl salt of a carboxylic acid such as vanadyl lactate or vanadyl citrate.

The plant may be treated by applying the application form of the composition to the foliage of the plant, applying the application form of the composition to earth around the plant, or irrigating the roots of the plant with the application form of the composition. Using one of these methods the application form of the composition is applied one or more times during the growth period of the plant. Preferably, the application form of the composition is applied only once during the growth period of the plant. The compositions are applied to achieve a treatment rate ranging from about 0.0006 to 0.6 kilograms of vanadium applied per hectare of growing plants.

Specifically, for fruit bearing plants the application form of the composition is applied to the plant from about 21 days before the start of the reproductive cycle of the plant to about 21 days after the start of the reproductive cycle of the plant. In this context, the start of the reproductive cycle of the plant is indicated by setting of blooms or a similar stage depending on the type of the plant.

In a preferred embodiment the application form of the composition is an aqueous solution which contains an effective concentration of vanadyl ions. The solution is prepared by dissolving an organic compound or complex of vanadium in water which provides a source of vanadyl ions. The solution is then sprayed onto the foliage or leaf surfaces of plants at the appropriate time during the growth period of the plants.

In another embodiment the application form of the composition is a solid in particulate form which includes an organic compound or complex of vanadium and is applied to earth around the plant. The solid particles of the composition are applied by spreading them around the plants at the appropriate time during the growth period. The action of water or rain then causes the solid particles to dissolve and generates a solution which has an effective concentration of vanadyl ions. The solution flows into the ground around the roots of the plants, and irrigates the roots of the plants.

Generally, the compositions which provide a source of vanadyl ions and methods of applying them are effective for all plants, but are particularly intended to promote the growth of monocots and dicots. Specifically, the compositions and methods of applying them may be used for plants such as cotton, wheat, corn, grain sorghum, grapes, or bell peppers, and similar plants. Vanadyl ions do not appear to be effective for promoting the growth of soybean, a legume.

The compositions of the invention and methods of applying them are particularly useful for promoting the growth of the fruits of many valuable and necessary food or other agronomic crops. For example, the yield of wheat from a particular plot of land will be increased by the use of the compositions of the invention and the methods for applying the compositions. (See Example 2). Likewise, the compositions and methods for applying the compositions may be used to increase the yield of cotton lint from a particular plot of land for growing cotton. (See Example 1).

DETAILED DESCRIPTION OF THE INVENTION

The compositions of the invention comprise a carrier agent and organic compounds or complexes of vanadium as an active ingredient which generate vanadyl ions when the composition is applied to a plant. Vanadyl ions are effective for promoting the growth of plants, especially plant fruits, when applied to plants during the growth period of the plants.

Vanadium is a transition metal which displays well-characterized valence states of $+2$ through $+5$ in solid compounds and in solution. Vanadium easily forms oxycations such as vanadyl ions $(VO)^{2+}$ which are composed of vanadium metal and oxygen. The valence state of vanadium in a vanadyl ion is $+4$. Many compounds or complexes which include vanadium may be used to generate the vanadyl ions.

For example, vanadium forms compounds or complexes with various organic compounds such as carboxylic acids. Carboxylic acids are characterized as organic compounds that contain at least one carboxyl group. The carboxyl group is represented chemically as:

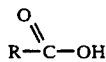

where R is a saturated or unsaturated organic group which includes one or more carbons.

Formic, acetic, propionic, and butyric acid are examples of carboxylic acids which contain one carboxyl group and form compounds or complexes with vanadyl ions. Likewise, oxalic, malonic, succinic, glutaric, adipic, maleic, and fumaric acid are examples of dicarboxylic acids which contain two carboxyl groups and form compounds or complexes with vanadyl ions. Further, other carboxylic acids with one or more carboxyl groups such as glycolic, lactic, glyceric, citric, tartaric, and malic acid form compounds or complexes with vanadyl ions. Organic compounds or complexes of vanadyl ions may also occur in polymeric form. The term "carboxylic acid" as used herein means any organic compound which includes one or more carboxyl groups, and specifically includes the compounds noted above.

Other compounds or complexes which contain vanadyl ions may also be used in the compositions of the invention. For example, a diketone such as acetylacetone forms vanadyl acetylacetonate which may be used in the compositions of the invention.

Some vanadium compounds are ineffective for promotion of plant growth, especially plant fruit growth. For example, vanadate compounds which generate the vanadate ion $(VO_2)^+$ in which vanadium has a $+5$ valence state are detrimental to plant growth. (See Example 8).

The compositions of the invention may be prepared in concentrate form or application form. For example, the composition may be made in solid particulate form which may be bagged and easily transported to a desired plant crop location. At the plant crop location the solid form may be mixed with water to create a solution which may be sprayed onto the foliage of plants. The solid particulate form of the composition may include an organic compound or complex of vanadium which may generate vanadyl ions when dissolved in the water. The solid particulate form would also include a conventional agricultural carrier agent in solid form.

Conventional liquid agricultural carrier agents may also be used in the various forms of the composition. Generally, the organic compound or complex of the vanadyl ions will be dissolved or dispersed in the liquid carrier agent. Preferably, water is used as the liquid carrier agent. Other conventional agricultural oils may also be used as the liquid carrier agent. For example, a liquid concentrate form of the composition may be prepared by dissolving or dispersing an amount of an organic compound or complex of vanadyl ions in water. The liquid concentrate is then containerized and transported to a plant crop location and mixed with more water to prepare an application form of the composition with an effective concentration of the vanadyl ions in solution. The application form of the composition is then sprayed onto the foliage of the plants.

Generally, the vanadyl ion compositions of the invention may be applied to any type of plant to promote growth. The term "promote growth" means improving the number, size, quantity, or quality of fruits that grow on the plants; and may additionally include increasing the amount or quality of the foliage. The term "promote growth" also encompasses characterizations of the effect of the composition on plants such as yield enhancer, fertilizer, and micro-nutrient. Plant fruit in this context includes any seed bearing organ of a plant such as the cotton boll of cotton, the kernel of wheat or corn, the grape of grapevines, or the bell pepper of pepper plants. The vanadyl ion compositions additionally improve the water use efficiency of plants as one aspect of promoting the growth of the plants.

The vanadyl ion compositions of the invention are particularly intended for use on monocots (monocotyledons) and dicots (dicotyledons). Monocots and dicots are the two varieties of seed-producing, flowering plants. For example; corn, wheat, rye, oats, barley, and rice are monocot grasses. Cotton is an example of dicot. An application of vanadyl ions increased the yield of harvested cotton from cotton plants, a dicot. (See Example 1). Likewise, an application of vanadyl ions increased the yield of harvested wheat from wheat plants, a monocot. (See Example 2).

The vanadyl ion compositions of the invention may also be applied to annual vegetables or crops, and perennial fruits or crops to promote their growth. For example, a vanadyl ion composition has improved the quality and amount of harvested bell peppers from pepper plants. (See Example 10). Further, a vanadyl ion composition improved the quality of grapes (i.e., the sugar content), harvested from grapevines for making wine. (See Example 9).

A composition of the invention proved ineffective for promoting the growth of soybeans, however. (See Example 5). The reason for this is not known, however soybean is a legume and none of the other plants tested were legumes.

Preferably, the vanadyl ion composition is applied to the plant during the growth period of the plant. The time and number of applications of the composition are dependent upon the type of the plant and the desired effect. For example, to promote fruit growth, the composition should be applied during the time period from shortly before the start of the reproductive stage of the plant to shortly after the start of the reproductive stage of the plant. The start of the reproductive stage of the plant is characterized by the setting of blooms, or a similar stage indicating the beginning of the fruit depending on the type of plant.

Preferably, the vanadyl ion composition is applied between about 21 days before the start of the reproductive stage of the plant to about 21 days after the start of the reproductive stage of the plant. For cotton, the preferred application time period is from 14 days prior to the setting of blooms to 7 days after the setting of the blooms. For any particular plant the optimal time for applying the vanadyl ion composition within the period of 21 days before to 21 days after the start of the reproductive stage may be determined using conventional techniques.

The vanadyl ion composition is applied one or more times during the growth period for the plant. Preferably, only one application is made during the growth period of the plant. The amount of vanadium applied is somewhat dependent on the type of plant being treated. Generally, the amount of composition applied should provide a total treatment for all applications ranging from about 0.0006 to 0.6 kilograms of vanadium applied per hectare of plants. Preferably, the amount of composition applied should provide a total treatment for all applications ranging from about 0.002 to 0.08 kilograms of vanadium applied per hectare of plants.

Different methods may be used to apply the vanadyl ion compositions to plants. For example, a liquid form of the composition may be applied to the leaves or foliage of plants. This may be accomplished using conventional agricultural spray devices. Both liquid and solid forms of the composition may be applied to earth surrounding plants. For example, conventional watering systems may be used to apply a liquid form of the composition to earth around plants. Further, the composition may be applied to the roots of the plants. For example, the liquid form of the composition may be injected into the ground around the roots of the plants by using underground pipes or hoses.

Preferably, a liquid form of the vanadyl ion composition is applied by spraying it on the foliage of the plants. The concentration of vanadyl ions in the liquid form of the composition for spraying should fall within a optimum range dependent on the plants. Preferably, when spraying the liquid form of the composition the vanadyl ion concentration in the liquid form of the composition should achieve a range from about 0.0006 to 60.0 grams of vanadium per liter of the liquid. The liquid form of the composition is then sprayed onto the plants at a rate ranging from 10 to 1000 liters of liquid per hectare of plants. This provides an effective treatment rate of vanadyl ions while avoiding high concentrations of vanadyl ions in the spray which might be harmful to the plants.

To maintain the vanadyl ions in the liquid form of the composition, it is necessary to control the pH of the composition. Otherwise the vanadyl ions might be converted to other noneffective vanadium ions such as vanadate ions. Generally, the application form of the composition should be maintained at a pH ranging from about 4 to 9 to maintain the vanadyl ions. Preferably, the pH is maintained in the range of about 6 to 8. Depending on the ingredients in the composition, the pH may be controlled by adding a buffering agent.

Other ingredients may also be added to the compositions to produce specific effects. For example, adhesives, thickeners, penetrating agents, spray oils, stabilizers, preservatives, sequestering agents, thixotropic agents, protective colloids, surface active agents, fertilizers, micro-nutrients, and pesticides may be added to the composition as desired.

EXAMPLE 1

Cotton plants were treated with solutions of vanadyl lactate. The cotton cultivar used was GSA-71. The solutions consisted of two concentration levels of vanadyl lactate in water: (1) In one solution vanadyl lactate was mixed with water in proportions of 1 part of vanadyl lactate by weight per 100 parts of water by weight; (2) in the second solution vanadyl lactate was mixed with water in proportions of 1 part of vanadyl lactate by weight per 1000 parts of water by weight. A surfactant "tween twenty" which is manufactured by Union Carbide was added to the vanadyl lactate solutions is amounts of 0.5 percent by volume. The surfactant was added to improve the spreading of the solution on the foliage and leaf surfaces of the cotton plants.

The solution was sprayed onto the foliage of the cotton in multiple applications from the time period before the first bloom until a time period after the first bloom. The cotton was planted on May 28, 1986. The first cotton plants emerged on Jun. 4, 1986. The first blooms occurred on Jul. 21, 1986. Harvest was conducted of the cotton crop after first frost. Table 1 indicates the results for this study.

TABLE 1

| Application Timing | Cotton Lint Yields | | |
|---|---|---|---|
| | Treatment Rate kg V/ha* | Yield kg/ha | % Increase Over Control |
| control | control | 969 | 0 |
| July 11, 18 | 0.076 | 1101 | 13.7 |
| July 11, 18, 24, 30 | 0.153 | 1111 | 14.7 |
| July 11, 18, 24, 30, Aug 1 | 0.229 | 1096 | 8.0 |
| July 11, 18, 24, 30, Aug 1, 19, 26 | 0.307 | 1094 | 13.0 |
| July 11, 18 | 0.763 | 1096 | 13.1 |
| July 11, 18, 24, 30 | 1.525 | 1182 | 22.0 |
| July 11, 18, 24, 30, Aug 1 | 2.288 | 1068 | 10.2 |

*ha = hectare

EXAMPLE 2

Wheat plants were treated with vanadyl lactate in a manner similar to the method used for treating cotton plants in Example 1. The application was made by spraying the wheat plants 10 days before they formed seed heads. Table 2 reports the results of this study.

TABLE 2

| | Wheat Yields | |
|---|---|---|
| Treatment Rate kg V/ha | Yield kg/ha | % Increase Over Control |
| control | 1490 | 0 |
| 0.028 | 1591 | 6.7 |
| 0.056 | 1747 | 17.2 |
| 0.112 | 1616 | 8.4 |

EXAMPLE 3

Corn plants were treated with vanadyl lactate in a manner similar to the method used for treating cotton plants in Example 1. The vanadyl lactate was applied at two different times: (1) when the tenth leaf was visible, and (2) when the tassel was exerted. Table 3 reports the results of this study.

TABLE 3

Corn Yields

| Treatment Rate kg V/ha | Application Timing | Yield kg/ha | % Increase Over Control |
|---|---|---|---|
| control | N/A | 11565 | 0 |
| 0.0056 | 10th leaf | 12071 | 4.4 |
| 0.028 | 10th leaf | 13547 | 17.1 |
| 0.056 | 10th leaf | 12613 | 9.1 |
| 0.0056 | tassel | 12234 | 5.8 |
| 0.028 | tassel | 12021 | 3.9 |
| 0.056 | tassel | 11635 | 0.6 |

EXAMPLE 4

Grain sorghum was treated with vanadyl lactate in a manner similar to the method used for treating cotton plants in Example 1. The vanadyl lactate was applied at two times: (1) when the tenth leaf was visible, and (2) during early bloom. Table 4 reports the results of this study.

TABLE 4

Grain Sorghum Yields

| Treatment Rate kg V/ha | Application Timing | Yield kg/ha | % Increase Over Control |
|---|---|---|---|
| control | control | 8056 | 0 |
| 0.0056 | 10th leaf | 8315 | 3.2 |
| 0.028 | 10th leaf | 8774 | 8.9 |
| 0.056 | 10th leaf | 8899 | 10.5 |
| 0.0056 | 1st bloom | 9301 | 15.5 |
| 0.028 | 1st bloom | 8802 | 9.9 |
| 0.056 | 1st bloom | 8475 | 5.2 |

EXAMPLE 5

Soybean plants were treated with vanadyl lactate in a manner similar to the method used for treating cotton plants in Example 1. Vanadyl lactate was applied at two times during the growth period: (1) early-during early-bloom, and (2) late-after the end of flowering. Table 5 reports the results of this study.

TABLE 5

Soybean Yields

| Treatment Rate kg V/ha | Application Timing | Yield kg/ha | % Increase Over Control |
|---|---|---|---|
| control | control | 2459 | 0 |
| 0.0056 | early | 2239 | −8.9 |
| 0.028 | early | 2366 | −3.8 |
| 0.056 | early | 2420 | −1.6 |
| 0.0056 | late | 2559 | +4.1 |
| 0.028 | late | 2380 | −3.2 |
| 0.056 | late | 2353 | −4.3 |

EXAMPLE 6

A study was conducted to determine the effect of surfactants in the vanadyl compositions used for treating plants, and to determine the effectiveness of different vanadium compounds. Table 6 reports the results of this study.

TABLE 6

Cotton Compound/Mixture Study

| Composition | Treatment Rate kg V/ha | Lint Yields (kg/ha) Field 1 | Lint Yields (kg/ha) Field 2 |
|---|---|---|---|
| control | control | 441 | 987 |
| v. lactate (.056 kg V/ha) + X77[1] | 0.056 | 507 | 1029 |
| v. lactate (.056 kg V/ha) | 0.056 | 457 | 1011 |
| v. lactate (pentoxide) + X77 | 0.056 | 443 | 1068 |
| v. citrate (pentoxide) + X77 | 0.056 | 464 | 1033 |
| v. acetate (pentoxide) + X77 | 0.056 | 472 | 944 |
| v. lactate + X77 + PIX[2] | 0.056 | 441 | 1066 |

[1]X77 is a surfactant manufactured by Ortho.
[2]PIX is a growth regulator manufactured by BASF.

The term (pentoxide) in the composition indicates that the vanadyl salt was derived from vanadium pentoxide. Field 1 was in Hockley County, Tex., and the cotton cultivar was Var. Ranger BB53. Field 2 was in Lynn County, Tex., and the cotton cultivar was Var. Paymaster HS26.

EXAMPLE 7

Table 7 reports a study of the effects of applying vanadyl lactate and vanadyl citrate using full and limited irrigation methods for applying the compositions. For the full irrigation method the ground around the plants was irrigated immediately before planting and twice after planting; once at the early bloom stage of the plant and then at the late bloom stage of the plant. For the limited irrigation method the ground around the plants was irrigated immediately before planting, and once after planting when the plant was at the early bloom stage.

TABLE 7

Cotton Compound Study of Irrigation Method

| Composition | Treatment Rate (kg V/ha) | Irrigation Method | Lint Yield kg/ha |
|---|---|---|---|
| control | control | control | 669 |
| v. lactate + X77 | 0.56 | full | 728 |
| v. citrate + X77 | 0.56 | full | 786 |
| control | control | control | 608 |
| v. lactate + X77 | 0.56 | limited | 688 |
| v. citrate + X77 | 0.56 | limited | 622 |

EXAMPLE 8

A study was conducted to determine the growth promotion effect of vanadium compounds that provide other vanadium and vanadyl ions. The study also determined the effect of lactic acid alone on promoting plant growth. Table 8 reports the results of this study.

TABLE 8

Cotton Compound Study

| Compound | Treatment Rate kg V/ha | Yield kg/ha | % Increase Over Control |
|---|---|---|---|
| control | control | 955 | 0 |
| vanadyl lactate | 0.056 | 1044 | 9.3 |
| vanadyl acetylacetonate | 0.056 | 1054 | 10.3 |
| sodium metavanadate | 0.056 | 881 | −7.7 |
| lactic acid | 0.000 | 1018 | 6.6 |

EXAMPLE 9

Eight year old Chenin Blanc grapevines were treated with vanadyl lactate at rates of about 0.006, 0.03, and 0.06 kilograms per hectare. Six plots with each plot containing four vines were used for each condition that was tested. The vanadyl lactate was applied by foliar spray to the grapevines at a rate of 100 liters of the vanadyl lactate solution per hectare.

Samples of the grapes were harvested from each of the plots, and the grapes were weighed and extracted. The volume of the extracted juice was then measured and the juice was analyzed for sugars (Brix), pH, and total titratable acids. Table 9 reports the results of this study.

TABLE 9

Grape Results

| Treatment Rate kg V/ha | g/Berry | ml/100 | Brix | pH | Titratable Acids |
|---|---|---|---|---|---|
| Sampled on July 26: | | | | | |
| control | 1.13 | 0.71 | 11.90 | 2.94 | 2.17 |
| 0.0056 | 1.19 | 0.65 | 13.77 | 3.01 | 1.99 |
| 0.028 | 1.12 | 0.69 | 13.50 | 2.97 | 1.88 |
| 0.056 | 1.24 | 0.77 | 14.77 | 3.03 | 1.79 |
| Sampled on August 2: | | | | | |
| control | 1.14 | 0.74 | 15.58 | 3.10 | 1.55 |
| Early application of composition: | | | | | |
| 0.0056 | 1.21 | 0.71 | 16.05 | 3.16 | 1.46 |
| 0.028 | 1.13 | 0.72 | 15.95 | 3.13 | 1.49 |
| 0.056 | 1.29 | 0.81 | 16.13 | 3.12 | 1.48 |
| Late application of composition: | | | | | |
| 0.0056 | 1.27 | 0.81 | 16.23 | 3.12 | 1.52 |
| 0.028 | 1.13 | 0.74 | 15.82 | 3.10 | 1.50 |
| 0.056 | 1.25 | 0.83 | 15.03 | 3.10 | 1.51 |
| Final harvest: | | | | | |
| control | 1.77 | 1.14 | 18.75 | 3.36 | 0.77 |
| Early application of composition: | | | | | |
| 0.0056 | 1.87 | 1.24 | 19.42 | 3.45 | 0.78 |
| 0.028 | 1.67 | 1.08 | 19.71 | 3.41 | 0.73 |
| 0.056 | 1.91 | 1.22 | 19.34 | 3.41 | 0.71 |
| Late application of composition: | | | | | |
| 0.0056 | 1.76 | 1.12 | 19.62 | 3.39 | 0.72 |
| 0.028 | 1.78 | 1.17 | 19.32 | 3.40 | 0.67 |
| 0.055 | 1.73 | 1.13 | 19.01 | 3.36 | 0.76 |

The early application of the composition was made when the grapes were at the 5 brix stage. The late application of the composition was made when the grapes were at the 12-14 brix stage.

EXAMPLE 10

Six plots of bell pepper plants which were twenty feet in length were treated with various concentrations of vanadyl lactate. Treatments were made twice, at first bloom and at first fruit set, during the growing period of the plants. The treatment mixture consisted of vanadyl lactate dissolved in water, and additionally 0.5% by volume of Ortho ® X-77 surfactant was added to the water. A control treatment consisting of only water and the Ortho ® X-77 surfactant was also used. The mixture was applied at a rate of 173 liters per hectare by spraying the mixture onto the foliage of the plants. Peppers were harvested from the plots, separated into USDA grades, and counted and weighed. Table 10 reports the results of this study.

TABLE 10

Bell Pepper Results

| Treatment Rate kg V/ha | Yield kg/ha | Fancy | US1 | US2 | Cull |
|---|---|---|---|---|---|
| control | 3886 | 23 | 64 | 13 | 0 |
| Application made at 1st bloom: | | | | | |
| 0.0056 | 4944 | 33 | 45 | 18 | 3 |
| 0.0028 | 3346 | 20 | 49 | 20 | 10 |
| 0.056 | 3371 | 32 | 47 | 20 | 1 |

TABLE 10-continued

Bell Pepper Results

| Treatment Rate kg V/ha | Yield kg/ha | Fancy | US1 | US2 | Cull |
|---|---|---|---|---|---|
| Application made at 1st fruit set | | | | | |
| 0.0056 | 4969 | 55 | 41 | 2 | 1 |
| 0.0028 | 4786 | 26 | 44 | 28 | 2 |
| 0.056 | 2041 | 20 | 56 | 18 | 5 |

EXAMPLE 11—PREPARATION METHOD 1.2 moles of lactic acid were added to a solution of 0.25 mole of vanadium pentoxide in a working volume of water. The working volume of water was dependent upon the amount needed to prepare the overall solution, keeping in mind that eventually more water would be added to increase the solution volume to 1 liter. The mixture of lactic acid, vanadium pentoxide, and water was stirred on a hot plate, while the temperature was raised to 70°-80° C.

In 30 minutes or less, the vanadium pentoxide and lactic acid reacted to form vanadyl lactate in its ionic form which includes vanadyl ions. The vanadyl ions were characterized by a dark blue color in the solution. The solution was then cooled to room temperature. The pH of the solution was acidic due to the lactic acid, and the pH was adjusted to approximately neutral (6-7 pH) by adding an appropriate amount of a 5 molar sodium hydroxide solution. Water was next added to the solution to increase the volume of the solution to 1 liter. This provided a vanadyl ion concentration of 0.50 mole per liter.

The examples and embodiments described above illustrate the invention. Changes and modifications can be made without departing from the scope of the invention. It is intended that such changes and modifications fall within the scope of the invention as defined by the appended claims. For example, other compounds of vanadium such as vanadyl tartrate may be used in the composition of the invention to provide vanadyl ions.

What is claimed is:

1. A method for promoting the lint yield of a fiber-producing plant comprising:
   treating the plant during a growth period of the plant with an amount of a composition comprising a vanadyl salt of a carboxylic acid, said composition being effective for promoting the lint yield of the plant.

2. The method of claim 1 wherein said vanadyl salt of a carboxylic acid is particularly effective for promoting the lint yield of the fruits of the plant.

3. The method of claim 1 wherein the plant is treated with the composition one or more times during the growth period of the plant.

4. The method of claim 1 wherein the plant is treated with the composition between about 21 days before the start of the reproductive stage of the plant to about 21 days after the start of the reproductive stage of the plant.

5. The method of claim 1 wherein the plant is treated by applying the composition to foliage of the plant.

6. The method of claim 1 wherein the plant is treated by applying the composition to earth around the plant.

7. The method of claim 1 wherein the plant is treated by irrigating roots of the plant with the composition.

8. The method of claim 1 wherein the plant is treated with the composition at a rate ranging from about 0.0028 to 0.6 kilograms of vanadium per hectare of plants.

9. The method of claim 1 wherein the plant is treated with the composition at a rate ranging from about 0.03 to 0.08 kilograms of vanadium per hectare of plants.

10. The method of claim 1 wherein the plant is cotton.

11. A method for promoting the lint yield of plant fruits of fiber-producing plants comprising:
treating the plant during a growth period for the plant with a composition comprising a vanadyl salt of a carboxylic acid dissolved or dispersed in a liquid carrier agent at a rate ranging from about 0.0028 to 0.6 kilograms of vanadium per hectare of the plants.

12. The method of claim 11 wherein the composition is applied once during the growth period of the plants.

13. The method of claim 11 wherein the plant is treated with the composition between about 21 days before the start of the reproductive stage of the plant to about 21 days after the start of the reproductive stage of the plant.

14. The method of claim 11 wherein the plant is treated by applying the composition to foliage of the plant.

15. The method of claim 11 wherein the plant is treated by applying the composition to earth around the plant.

16. The method of claim 11 wherein the plant is treated by irrigating roots of the plant with the composition.

17. The method of claim 1 wherein the carboxylic acid is formic, acetic, propionic, butyric, glycolic, lactic, glyceric, citric, tartaric, malic, adipic, oxalic, malonic, succinic, maleic, fumaric, glutaric, or acetylacetic acid.

* * * * *